United States Patent
Nag et al.

(10) Patent No.: US 11,823,792 B2
(45) Date of Patent: *Nov. 21, 2023

(54) PEER COMMUNITY BASED ANOMALOUS BEHAVIOR DETECTION

(71) Applicant: CareFusion 303, Inc., San Diego, CA (US)

(72) Inventors: Abhikesh Nag, San Diego, CA (US); Cynthia Yamaga, Oceanside, CA (US)

(73) Assignee: CareFusion 303, Inc., San Diego, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 17/539,490

(22) Filed: Dec. 1, 2021

(65) Prior Publication Data
US 2022/0093239 A1    Mar. 24, 2022

Related U.S. Application Data

(63) Continuation of application No. 16/403,174, filed on May 3, 2019, now Pat. No. 11,222,721.
(Continued)

(51) Int. Cl.
*G16H 40/20* (2018.01)
*G06Q 10/06* (2023.01)
(Continued)

(52) U.S. Cl.
CPC ......... *G16H 40/20* (2018.01); *G06Q 10/0633* (2013.01); *G06Q 10/063114* (2013.01); *G06Q 50/22* (2013.01); *H04L 63/1425* (2013.01)

(58) Field of Classification Search
CPC ........... G16H 40/20; G06Q 10/063114; G06Q 10/0633; G06Q 50/22; H04L 63/1425
See application file for complete search history.

(56) References Cited

U.S. PATENT DOCUMENTS

| 5,945,651 A | 8/1999 | Chorosinski et al. |
| 6,650,964 B2 | 11/2003 | Spano, Jr. et al. |

(Continued)

FOREIGN PATENT DOCUMENTS

| AU | 2017 279 693 A1 | 1/2018 |
| CA | 2 636 115 C | 6/2014 |

(Continued)

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS) Proceedings*, 43-47. Doi: 10.1109/VECIMS.2012.6273190.

(Continued)

*Primary Examiner* — Maroun P Kanaan
(74) *Attorney, Agent, or Firm* — Mintz Levin Cohn Ferris Glovsky and Popeo, P.C.

(57) ABSTRACT

A peer network may include nodes corresponding to different clinicians. An edge may interconnect the two nodes based on the corresponding clinicians sharing at least one common attribute such as for example, treating the same patients and/or interacting with the same medical devices. A machine-learning model may be applied to identify, in the peer network, one or more peer communities of clinicians. The activity pattern of a clinician may be compared to the activity patterns of other clinicians in the same peer community to determine whether that clinician exhibits anomalous behavior. An investigative workflow may be triggered when the clinician is determined to exhibit anomalous behavior. The investigative workflow may include generating an alert, activating surveillance devices, and/or isolating medication accessed by the clinician.

19 Claims, 7 Drawing Sheets

Related U.S. Application Data

(60) Provisional application No. 62/667,409, filed on May 4, 2018.

(51) Int. Cl.
*G06Q 10/0631* (2023.01)
*G06Q 10/0633* (2023.01)
*G06Q 50/22* (2018.01)
*H04L 9/40* (2022.01)

(56) References Cited

U.S. PATENT DOCUMENTS

| | | | |
|---|---|---|---|
| 6,671,579 B2 | 12/2003 | Spano, Jr. et al. | |
| 6,842,736 B1 | 1/2005 | Brzozowski | |
| 6,868,344 B1 | 3/2005 | Nelson | |
| 7,119,689 B2 | 10/2006 | Mallett et al. | |
| 7,184,897 B2 | 2/2007 | Nelson | |
| 7,275,645 B2 | 10/2007 | Mallett et al. | |
| 7,303,081 B2 | 12/2007 | Mallett et al. | |
| 7,311,207 B2 | 12/2007 | Mallett et al. | |
| 7,318,529 B2 | 1/2008 | Mallett et al. | |
| 7,562,025 B2 | 7/2009 | Mallett et al. | |
| 8,147,479 B1 | 4/2012 | Wach et al. | |
| 8,195,328 B2 | 6/2012 | Mallett et al. | |
| 8,280,550 B2 | 10/2012 | Levy et al. | |
| 8,319,669 B2 | 11/2012 | Weller | |
| 8,357,114 B2 | 1/2013 | Poutiatine et al. | |
| 8,595,021 B2 | 11/2013 | Mallett et al. | |
| 8,606,596 B1 | 12/2013 | Bochenko et al. | |
| 8,725,532 B1 | 5/2014 | Ringold | |
| 8,738,177 B2 | 5/2014 | van Ooyen et al. | |
| 8,768,724 B2 | 7/2014 | Whiddon et al. | |
| 8,905,964 B2 | 12/2014 | Poutiatine et al. | |
| 9,158,892 B2 | 10/2015 | Levy et al. | |
| 9,202,052 B1 | 12/2015 | Fang et al. | |
| 9,227,025 B2 | 1/2016 | Butterfield et al. | |
| 9,354,178 B2 | 5/2016 | Lee | |
| 9,427,520 B2 | 8/2016 | Batch et al. | |
| 9,456,958 B2 | 10/2016 | Reddy et al. | |
| 9,523,635 B2 | 12/2016 | Tilden | |
| 9,636,273 B1 | 5/2017 | Harris | |
| 9,752,935 B2 | 9/2017 | Marquardt et al. | |
| 9,796,526 B2 | 10/2017 | Smith et al. | |
| 9,817,850 B2 | 11/2017 | Dubbels et al. | |
| 9,836,485 B2 | 12/2017 | Dubbels et al. | |
| 9,842,196 B2 | 12/2017 | Utech et al. | |
| 9,881,129 B1 | 1/2018 | Cave | |
| 9,958,324 B1 | 5/2018 | Marquardt et al. | |
| 10,032,344 B2 | 7/2018 | Nelson et al. | |
| 10,101,269 B2 | 10/2018 | Judge et al. | |
| 10,187,288 B2 | 1/2019 | Parker et al. | |
| 10,209,176 B2 | 2/2019 | Proskurowski et al. | |
| 10,241,038 B2 | 3/2019 | Nishimura et al. | |
| 10,249,153 B2 | 4/2019 | Nelson et al. | |
| 10,309,832 B2 | 6/2019 | Marquardt et al. | |
| 10,345,242 B2 | 7/2019 | Zhao et al. | |
| 10,832,207 B2 | 11/2020 | Vahlberg et al. | |
| 11,116,892 B2 | 9/2021 | Brady et al. | |
| 11,147,914 B2 | 10/2021 | Estes | |
| 2003/0158751 A1 | 8/2003 | Suresh et al. | |
| 2008/0059226 A1 | 3/2008 | Melker et al. | |
| 2008/0082360 A1 | 4/2008 | Bailey et al. | |
| 2008/0140715 A1 | 6/2008 | Hakos | |
| 2008/0288430 A1 | 11/2008 | Friedlander et al. | |
| 2008/0306796 A1 | 12/2008 | Zimmerman et al. | |
| 2008/0319795 A1 | 12/2008 | Poteet et al. | |
| 2009/0083231 A1* | 3/2009 | Eberholst | G16H 10/60 |
| | | | 707/999.102 |
| 2009/0160646 A1 | 6/2009 | Mackenzie et al. | |
| 2011/0016110 A1 | 1/2011 | Egi et al. | |
| 2011/0161108 A1 | 6/2011 | Miller et al. | |
| 2012/0226447 A1 | 9/2012 | Nelson et al. | |
| 2012/0265336 A1 | 10/2012 | Mallett et al. | |
| 2012/0325330 A1 | 12/2012 | Prince et al. | |
| 2013/0002429 A1 | 1/2013 | Johnson | |
| 2013/0018356 A1 | 1/2013 | Prince et al. | |
| 2013/0070090 A1 | 3/2013 | Bufalini et al. | |
| 2013/0144254 A1 | 6/2013 | Amirouche et al. | |
| 2013/0253291 A1 | 9/2013 | Dixon et al. | |
| 2013/0253700 A1 | 9/2013 | Carson et al. | |
| 2013/0282392 A1 | 10/2013 | Wurm | |
| 2013/0325727 A1 | 12/2013 | MacDonell et al. | |
| 2014/0074284 A1 | 3/2014 | Czaplewski et al. | |
| 2014/0081652 A1* | 3/2014 | Klindworth | G06Q 10/0635 |
| | | | 705/2 |
| 2014/0149131 A1 | 5/2014 | Bear et al. | |
| 2014/0249776 A1 | 9/2014 | King et al. | |
| 2014/0277707 A1 | 9/2014 | Akdogan et al. | |
| 2014/0375324 A1 | 12/2014 | Matsiev et al. | |
| 2015/0038898 A1 | 2/2015 | Palmer et al. | |
| 2015/0061832 A1 | 3/2015 | Pavlovic et al. | |
| 2015/0081324 A1* | 3/2015 | Adjaoute | G06Q 40/08 |
| | | | 705/2 |
| 2015/0109437 A1 | 4/2015 | Yang et al. | |
| 2015/0161558 A1 | 6/2015 | Gitchell et al. | |
| 2015/0221086 A1 | 8/2015 | Bertram | |
| 2015/0272825 A1 | 10/2015 | Lim et al. | |
| 2015/0286783 A1 | 10/2015 | Kumar et al. | |
| 2015/0294079 A1 | 10/2015 | Bergougnan | |
| 2015/0323369 A1 | 11/2015 | Marquardt | |
| 2015/0339456 A1 | 11/2015 | Sprintz | |
| 2015/0362350 A1 | 12/2015 | Miller et al. | |
| 2016/0034274 A1 | 2/2016 | Diao et al. | |
| 2016/0062371 A1 | 3/2016 | Davidian et al. | |
| 2016/0117478 A1 | 4/2016 | Hanina et al. | |
| 2016/0161705 A1 | 6/2016 | Marquardt et al. | |
| 2016/0166766 A1 | 6/2016 | Schuster et al. | |
| 2016/0259911 A1 | 9/2016 | Koester | |
| 2016/0283691 A1 | 9/2016 | Ali | |
| 2017/0017760 A1 | 1/2017 | Freese et al. | |
| 2017/0032102 A1 | 2/2017 | Skoda | |
| 2017/0076065 A1 | 3/2017 | Darr et al. | |
| 2017/0083681 A1 | 3/2017 | Sprintz et al. | |
| 2017/0103203 A1 | 4/2017 | Sharma et al. | |
| 2017/0108480 A1 | 4/2017 | Clark et al. | |
| 2017/0109480 A1 | 4/2017 | Vahlberg | |
| 2017/0109497 A1 | 4/2017 | Tribble et al. | |
| 2017/0120035 A1 | 5/2017 | Butterfield et al. | |
| 2018/0028408 A1 | 2/2018 | Li et al. | |
| 2018/0039736 A1 | 2/2018 | Williams | |
| 2018/0046651 A1 | 2/2018 | Dubbels et al. | |
| 2018/0157803 A1 | 6/2018 | Mirov | |
| 2018/0192942 A1 | 7/2018 | Clark et al. | |
| 2018/0231415 A1 | 8/2018 | Marquardt et al. | |
| 2018/0247703 A1 | 8/2018 | D'Amato | |
| 2018/0259446 A1 | 9/2018 | Coffey et al. | |
| 2018/0299375 A1 | 10/2018 | Young et al. | |
| 2018/0330824 A1 | 11/2018 | Athey et al. | |
| 2018/0365386 A1 | 12/2018 | Vanderveen | |
| 2019/0088354 A1 | 3/2019 | Yanowitz et al. | |
| 2019/0117883 A1 | 4/2019 | Abrams et al. | |
| 2019/0124118 A1* | 4/2019 | Swafford | H04L 63/1408 |
| 2019/0180862 A1 | 6/2019 | Wisser et al. | |
| 2019/0244699 A1 | 8/2019 | Loebig et al. | |
| 2019/0247703 A1 | 8/2019 | Welde et al. | |
| 2019/0341142 A1 | 11/2019 | Nag et al. | |
| 2020/0098474 A1 | 3/2020 | Vanderveen | |
| 2020/0219611 A1 | 7/2020 | Nag et al. | |
| 2020/0222627 A1 | 7/2020 | Guerra et al. | |
| 2020/0230316 A1 | 7/2020 | Guerra et al. | |
| 2021/0133201 A1 | 5/2021 | Tribble et al. | |
| 2021/0308385 A1 | 10/2021 | Nisha et al. | |

FOREIGN PATENT DOCUMENTS

| | | |
|---|---|---|
| CA | 2 848 274 C | 9/2016 |
| EP | 1 973 593 B1 | 4/2013 |
| EP | 1 593 076 B1 | 10/2019 |
| WO | WO-2006/034367 A2 | 3/2006 |
| WO | WO-2010/058796 A1 | 5/2010 |
| WO | WO-2011/039676 A2 | 4/2011 |
| WO | WO-2014/055925 A1 | 4/2014 |

(56) References Cited

FOREIGN PATENT DOCUMENTS

| WO | WO-2015/187682 A1 | 12/2015 |
| WO | WO-2019/028004 A1 | 2/2019 |
| WO | WO-2019/031331 A1 | 2/2019 |

OTHER PUBLICATIONS

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

Neuman, M.R. et al. (May 13, 2012), "Advances in Medical Devices and Medical Electronics," in Proceedings of the IEEE, vol. 100, No. Special Centennial Issue, pp. 1537-1550,doi: 10.1109/JPROC.2012.2190684.

Qui et al. (2016) "A survey of machine learning for big data processing." *EURASIP Journal on Advances in Signal Processing*, Article No. 67, 16 pages.

Shishvan, O. Rajabi et al. (2018). "Machine Intelligence in Healthcare and Medical Cyber Physical Systems: A Survey." *IEEE Access*. vol. 6, 46419-46494. doi: 10.1109/ACCESS.2018.2866049.

Uniyal, D. et al. (Nov. 7, 2014), "Pervasive Healthcare—A Comprehensive Survey of Tools and Techniques," arXiv:1411.1821v1, 48 pages.

Yang, J., McAuley, J.J., & Leskovec, J. (2013). "Community Detection in Networks with Node Attributes." 2013 IEEE 13th International Conference on Data Mining, 1151-1156.

Yaniv, Z. et al. (Oct. 1, 2016). "The National Library of Medicine Pill Image Recognition Challenge: An Initial Report." *2016 OCT IEEE Applied Imagery Pattern Recognition Workshop, (AIPR)*, 1-9. Doi: 10.1109/AIPR.2016.8010584.

Zhan, A. et al. (Jan. 5, 2016) "High Frequency Remote Monitoring of Parkinson's Disease via Smartphone: Platform Overview and Medication Response Detection," Retrieved Apr. 29, 2021. 12 pages.

\* cited by examiner

PEER COMMUNITY BASED ANOMALOUS BEHAVIOR DETECTION

RELATED APPLICATION

This application is a continuation application of Ser. No. 16/403,174 filed May 3, 2019, entitled "PEER COMMUNITY BASED ANOMALOUS BEHAVIOR DETECTION," which claims priority to U.S. Provisional Application No. 62/667,409 filed May 4, 2018, entitled "ADDRESSING ANOMALOUS BEHAVIOR AMONG PEER GROUPS OF CLINICIANS," the disclosures of which are incorporated herein by reference in their entirety.

TECHNICAL FIELD

The subject matter described herein relates generally to complex networks and more specifically to a peer community based technique for detecting anomalous behavior.

BACKGROUND

Diversion may refer to the transfer of a controlled substance to a third party who is not legally authorized to receive, possess, and/or consume the controlled substance. High-value and/or controlled prescription medications, notably opioids, may be especially prone to diversion. For instance, prescription pain medications may be diverted while being loaded into and/or retrieved from a dispensing cabinet. Some prescription pain medications, such as morphine, hydromorphone, fentanyl, and/or the like, may be administered to a patient via a pump such as, for example, a patient-controlled analgesic (PCA) pump, that is capable of holding more doses of the pain medication than is needed by the patient. These extra doses of pain medication may be susceptible to being diverted by the clinicians tending the patient. For example, some of the pain medication may be removed before being loaded into the pump. Alternatively and/or additionally, any pain medication that remains in the pump may be held back instead of properly disposed of at a wasting site.

SUMMARY

Systems, methods, and articles of manufacture, including computer program products, are provided for identifying communities of clinicians and detecting anomalous behavior within the communities of clinicians. In one aspect, there is provided a system. The system may include at least one data processor and at least one memory. The at least one memory may store instructions that result in operations when executed by the at least one data processor. The operations may include: identifying a first peer community in a peer network by at least applying a machine-learning model trained to identify one or more peer communities present in the peer network, the peer network including a plurality of clinicians, and the first peer community including a first clinician and a second clinician from the plurality of clinicians based at least on the first clinician and the second clinician sharing at least one common attribute; comparing a first activity pattern of the first clinician to a second activity pattern of the second clinician; determining, based at least on the comparison between the first activity pattern of the first clinician and the second activity pattern of the second clinician, that the first clinician exhibits anomalous behavior; and in response to determining that the first clinician exhibits anomalous behavior, triggering an investigative workflow at one or more data systems.

In some variations, one or more features disclosed herein including the following features can optionally be included in any feasible combination. The at least one common attribute may include one or more of a same patient treated by the first clinician and the second clinician.

In some variations, the at least one common attribute may include one or more of a same medical device or medical devices located in a same care area that the first clinician and the second clinician interact with.

In some variations, the at least one common attribute may include one or more of: a prescription order, a clinician role, a shift, a supervisor, an educational background, training, an assigned care area, a medical protocol, and a physical layout of facility.

In some variations, the peer network may be generated to include a first node corresponding to the first clinician and a second node corresponding to the second clinician. The peer network may further include an edge interconnecting the first node and the second node based at least on the first clinician and the second clinician sharing the at least one common attribute. The peer network may be generated based at least on a plurality of transaction records generated by the one or more data systems in response to the first clinician or the second clinician interacting with the one or more data systems. The plurality of transaction records may include at least one transaction record that is generated in response to the first clinician interacting with a medical device to retrieve, administer, or dispose of a medication. The at least one transaction record may include at least one of: a timestamp, a first identifier of the first clinician, a second identifier of a patient associated with the medication, a third identifier of the medication, a fourth identifier of the medical device, a location identifier of the medical device, or a quantity of the medication.

In some variations, the investigative workflow may include sending, to a client, an alert indicating the first clinician as exhibiting anomalous behavior.

In some variations, the investigative workflow may include activating one or more surveillance devices in response to the first clinician interacting with a medical device and/or isolating medication accessed by the first clinician.

In some variations, the machine-learning model may include at least one of: a neural network, minimum cut, hierarchical clustering, Girvan-Newman, modularity maximization, or clique detection.

In some variations, the edge may be associated with a weight corresponding to a quantity of common attributes shared between the first clinician and the second clinician.

In some variations, the comparing may include assigning, to the first clinician, a rank corresponding to how much the first activity pattern of the first clinician deviates from a norm of the first peer community. The first clinician may be determined to exhibit anomalous behavior based at least on the rank assigned to the first clinician being above or below a threshold value. The norm may include an expected norm determined based at least on the first activity pattern of the first clinician and the second activity pattern of the second clinician. The norm may include a synthetic norm determined based on data in addition to the first activity pattern of the first clinician and/or the second activity pattern of the second clinician.

In some variations, a second peer community present in the peer network may be identified by at least applying the machine learning. The comparison to determine whether the first clinician exhibits anomalous behavior may exclude a third activity pattern of a third clinician included in the second peer community.

In another aspect, there is provided a non-transitory computer readable medium that stores instructions. The instructions may cause operations when executed by at least one data processor. The operations may include: identifying a first peer community in a peer network by at least applying a machine-learning model trained to identify one or more peer communities present in the peer network, the peer network including a plurality of clinicians, and the first peer community including a first clinician and a second clinician from the plurality of clinicians based at least on the first clinician and the second clinician sharing at least one common attribute; comparing a first activity pattern of the first clinician to a second activity pattern of the second clinician; determining, based at least on the comparison between the first activity pattern of the first clinician and the second activity pattern of the second clinician, that the first clinician exhibits anomalous behavior; and in response to determining that the first clinician exhibits anomalous behavior, triggering an investigative workflow at one or more data systems.

In some variations, one or more features disclosed herein including the following features can optionally be included in any feasible combination. The operations may further include: identifying a second peer community present in the peer network by at least applying the machine learning, the comparison to determine whether the first clinician exhibits anomalous behavior excluding a third activity pattern of a third clinician included in the second peer community.

In another aspect, there is provided an apparatus for performing an investigative workflow. The apparatus may include at least one data processor and at least one memory. The at least one memory may store instructions that result in operations when executed by the at least one data processor. The operations may include: receiving an indication identifying a first clinician as exhibiting anomalous behavior, the first clinician being part of a peer community in a peer network including a plurality of clinicians, the peer community being identified by at least applying a machine-learning model trained to identify one or more peer communities present in the peer network, and the first clinician being identified as exhibiting anomalous behavior based at least on a comparison between a first activity pattern of the first clinician and a second activity pattern of a second clinician in the peer community; and in response to the indication, initiating an investigative workflow that includes activating one or more surveillance devices in response to the first clinician interacting with the apparatus and/or isolating medication accessed by the first clinician.

In some variations, one or more features disclosed herein including the following features can optionally be included in any feasible combination. The apparatus may be an infusion pump or an automated dispensing device.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to identifying peer communities of clinicians in order to detect the occurrence of anomalous behavior, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
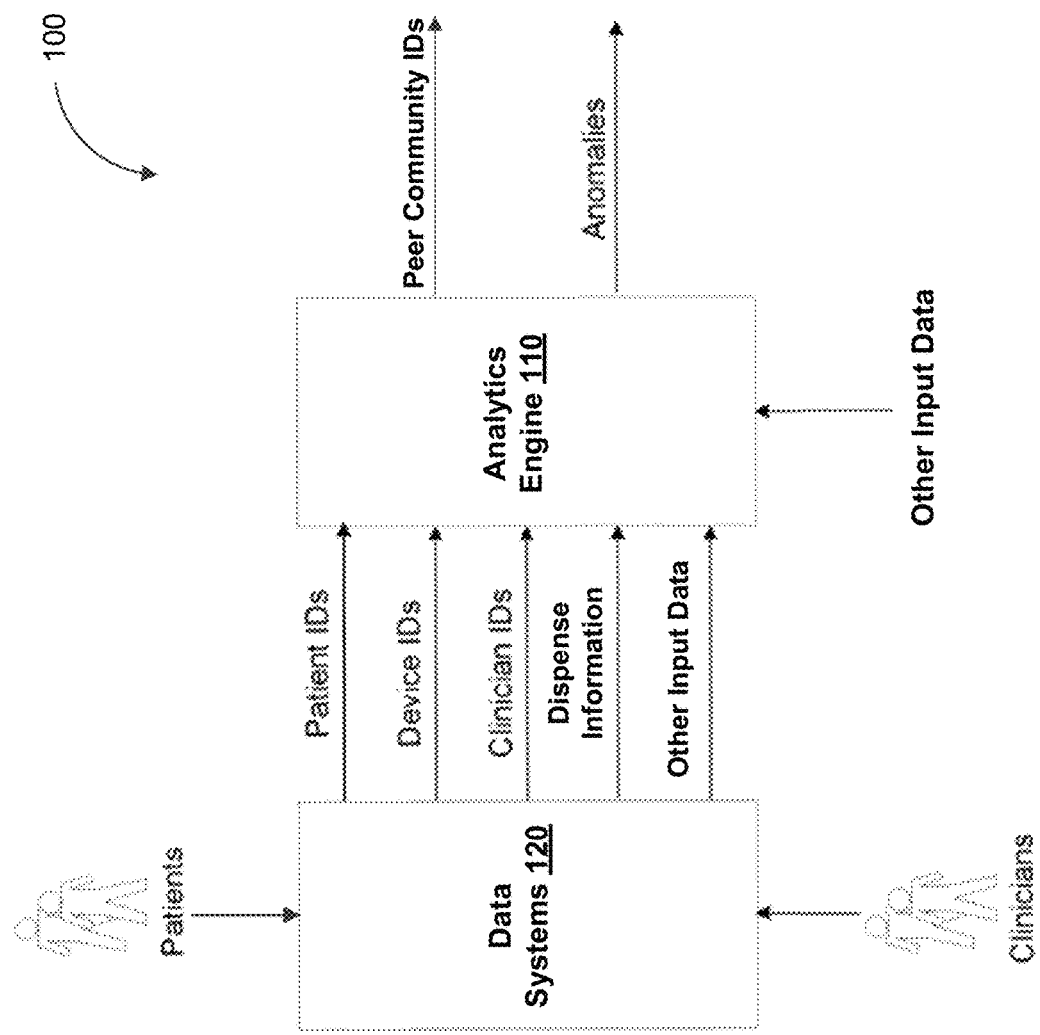
FIG. 1 depicts a block diagram illustrating a clinician tracking system, in accordance with some example embodiments.

Diversion of a medication may occur at any point in time including, for example, during the shipping, receiving, stocking, dispensing, administration, and/or wasting of the medication. Prescription pain medications may be especially prone to diversion due to a lack of sufficient custodial oversight during, for instance, the shipping, receiving, stocking, dispensing, administration, and/or wasting of the prescription pain medication. For example, dispensing cabinets at medical facilities may be accessible to multiple clinicians.

Moreover, different clinicians may be responsible for the dispensing, administration, and wasting of the medication. Thus, even when diversion is detected, it may be difficult to determine when the diversion actually occurred and identify the clinicians responsible for the diversion. As such, in some example embodiments, an analytics engine may detect diversion as well as identify the clinicians responsible for the diversion by at least identifying clinicians who exhibit anomalous behavior. For example, the analytics engine may determine that a clinician exhibits anomalous behavior by at least comparing activity data associated with the clinician against activity data associated with one or more other clinicians. The clinician may be determined to exhibit anomalous behavior if, for example, the activity data associated with the clinician include activity patterns that are inconsistent with the activity patterns present in the activity data of other clinicians. As used herein, a clinician may refer to a medical personnel having at least some access to a controlled substance including, for example, a doctor, a nurse, a pharmacist, a pharmacy technician, an imaging specialist, and/or the like.

At least some differences in activity patterns may be attributable to legitimate causes instead of illicit acts such as diversion. Thus, the analytics engine may be prone to false positives and/or false negatives if the analytics engine compares activity data associated with clinicians whose activity patterns may be dissimilar due to legitimate causes. For instance, an oncology nurse and a nurse working in neonatal intensive care unit may exhibit different activity patterns (e.g., in the dispensing, administration, and/or wasting of medications) because they treat patients with different conditions and medical needs. Likewise, a permanent nurse, a float nurse, a supplemental nurse, a student nurse, and a charge nurse may also exhibit different activities patterns because of differences in assigned shifts, care areas (e.g., medical-surgical, intensive care, emergency, infusion center, non-acute, outpatient, observation, and/or the like), facility, and/or tasks. As such, in some example embodiments, instead of comparing the activity data of different clinicians indiscriminately, the analytics engine may be configured to identify one or more peer communities of clinicians. Each peer community may be occupied by clinicians sharing sufficiently similar attributes such that the clinicians in the same peer community should also exhibit the same and/or similar activity patterns. Accordingly, to determine whether a clinician exhibits anomalous behavior, the analytics engine may compare the activity data associated with the clinician with the activity data of other clinicians in the same peer community. The analytics engine may determine that the clinician exhibits anomalous behavior if the activity patterns of the clinician deviate from the activity patterns of clinicians in the same peer community.

In some example embodiments, the analytics engine may apply a machine learning model such as, for example, a neural network, trained to identify one or more peer communities of clinicians. Peer communities of clinicians may also be identified by applying alternate techniques including, for example, minimum cut, hierarchical clustering, Girvan-Newman, modularity maximization, clique detection, and/or the like. The one or more peer communities of clinicians may be identified based on attributes that are highly correlated with activity patterns. For example, the peer communities of clinicians may be identified based on the patients treated by each clinicians because clinicians who treat the same patients should also exhibit the same and/or similar activity patterns. Alternatively and/or additionally, the peer communities of clinicians may be identified based on inter- actions with one or more medical devices such as, for example, dispensing cabinets, infusion pumps, wasting stations, and/or the like. Since clinicians operating in close proximity (e.g., in the same care area and/or the like) should exhibit the same and/or similar activity patterns, the location of medical devices may impose a geographical constraint on membership in each peer community. Nevertheless, it should be appreciated that an attribute and/or combination of attributes directly or indirectly detectable by the analytics engine may be used to identify different peer communities of clinicians. For example, peer communities may also be identified based on same and/or similar prescription orders, clinician roles, shifts, supervisors, educational background, training, assigned care areas, relevant medical protocols, physical layout of facilities and/or the like. Communities may additionally or alternatively be identified based on treatment of patients progressing through a common course of care within or across care areas including, for example, transitions between two common care areas, patient's duration within a care area, timing between care area transitions, and/or the like. Moreover, it should be appreciated that membership in the peer communities may remain dynamic as the attributes associated with each clinician may change over time. For instance, a clinician may be added to and/or removed from a peer community when the clinician starts or stops treating a particular patient.

FIG. 1 depicts a system diagram illustrating a clinician tracking system 100, in accordance with some example embodiments. Referring to FIG. 1, the clinician tracking system 100 may include an analytics engine 110 that is communicatively coupled with one or more data systems 120, which may include medical devices such as, for example, dispensing cabinets, infusion pumps, wasting stations, and/or the like. As shown in FIG. 1, the one or more data systems 120 may collect data that arise from clinicians interacting with the one or more data systems 120 including, for example, patient identifiers, devices identifiers, clinician identifiers, and/or the like. For instance, each of the one or more data systems 120 may be configured to generate a transaction record in response to an interaction with a clinician. For example, a clinician dispensing a medication from a dispensing cabinet may trigger the generation of a transaction record that includes a timestamp, a clinician identifier of the clinician, a device identifier of the dispensing cabinet, a patient identifier of a patient prescribed the medication, an identifier of the medication retrieved from the dispensing cabinet, a quantity of the medication retrieved from the medication cabinet, a location identifier, and/or the like. An example dispensing cabinet is described in U.S. Pat. No. 8,195,328, which is commonly owned and hereby incorporated by reference in its entirety. Alternatively and/or additionally, a clinician using an infusion pump to administer a medication to a patient may trigger the generation of a transaction record that includes a timestamp, a clinician identifier of the clinician, a device identifier of the infusion pump, a patient identifier of the patient receiving the medication, an identifier of the medication being administered to the patient, a quantity of the medication being administered to the patient, a location identifier, and/or the like. One example of an infusion pump is described in U.S. Pat. No. 9,227,025, which is commonly owned and hereby incorporated by reference in its entirety. It should be appreciated that the one or more data systems 120 may also provide non-transactional data. For instance, the one or more data systems 120 may provide electronic medical records (EMRs), which may include a patient's history including, for example, past opioid use and/or the like. While the act of creating, updating, and/or retrieving an electronic medical record may generate a timestamp transaction record, the electronic medical record itself is not a transaction record.

The analytics engine 110 may receive, from the one or more data systems 120, a plurality of input data including, for example, patient identifiers, devices identifiers, clinician identifiers, medication identifiers, prescription order identifiers, inventory information, shift identifiers, location tracking identifiers, electronic health record (EHR) identifiers, and/or the like. It should be appreciated that the input data from the one or more data systems 120 may include at least a portion of the transaction records that are generated in response to interactions with different clinicians. Moreover, the input data from the one or more data systems 120 may correspond to attributes that may be used to identify communities of clinicians. Accordingly, in some example embodiments, the analytics engine 110 may determine, based at least on the input data received from the one or more data systems 120, peer communities of clinicians, each of which being associated with a peer community identifier. Clinicians in the same peer community may be associated with sufficiently similar attributes such that the clinicians in the same peer community should also exhibit the same and/or similar activity patterns. Contrastingly, clinicians in different peer communities may be associated with different attributes that give rise to legitimate discrepancies in the activity patterns of the clinicians in different peer communities.

For example, the analytics engine 110 may identify, based at least on the input data received from the one or more data systems 120, peer communities of clinicians who treat the same patients. Alternatively and/or additionally, the analytics engine 110 may identify, based at least on the input data received from the one or more data systems 120, peer communities of clinicians who interact with the same medical devices and/or medical devices in a same care area. As used herein, a care area may refer to an area in a specific medical facility that is designated based on function and/or location. For instance, a facility such as a hospital may include a plurality of care areas such as, for example, medical-surgical, intensive care, emergency, observation, non-acute, infusion center, outpatient, and/or the like. It should be appreciated that the condition of a patient may be inferred based at least on the care area occupied by the patient. The condition of a patient may also be inferred based on the medication being administered to the patient. Clinicians treating patients with in the same and/or similar conditions should exhibit the same and/or similar activity patterns. As such, in addition to a geographical constraint, the location of medical devices being within a certain care unit may further refine membership in each peer community based on the condition of the patients that are being treated by the clinicians in each peer community.

As noted, clinicians in the same peer community should exhibit the same and/or similar activity patterns while clinicians in different peer communities may exhibit different activity patterns. Such similarities as well as disparities may be attributable to a variety of underlying causes. For example, the same patients and/or patients in the same care area may exhibit the same and/or similar needs for medication. Accordingly, the activity patterns of clinicians treating the same patients and/or operating in the same care area should be the same and/or similar in terms of the types and/or the quantities of the medication that each clinician retrieves from a dispensing cabinet, administers through an infusion pump, and/or disposes of at a wasting station. Alternatively and/or additionally, a same and/or similar treatment protocol may apply to the same patients and/or patients in the same care area. For instance, clinicians in one care area may be permitted to administer multiple doses of a medication before disposing unused medication at a wasting station whereas clinicians in another care area may only be permitted to administer a single dose of the medication before the unused medication are disposed of at a wasting station. The activity patterns of clinicians treating the same patients and/or operating in the same care area may therefore also reflect the corresponding treatment protocol. Furthermore, the design of a care area (e.g., layout, quantity of available medical devices, and/or the like) may give rise to similarities in the activity patterns of clinicians operating in that care area. For example, the activity patterns of a clinician operating in the care area may reflect the distance the clinician must travel in order to access a patient and/or a medical device in the care area.

Because clinicians in the same peer community should exhibit the same and/or similar activity patterns, the analytics engine 110 may determine whether a clinician exhibits anomalous behavior by comparing the activity patterns of the clinician to the activity patterns of other clinicians in the same peer community. The activity patterns of the clinician may include a series of transaction records which, as noted, may be generated when the clinician interacts with the one or more data systems 120.

In some example embodiments, the series of transaction records may be divided temporally to correspond, for example, to the shifts (e.g., time periods of work) associated with the clinician. The analytics engine 110 may determine that the clinician exhibits anomalous behavior if the activity patterns of the clinician deviate from the activity patterns of other clinicians in the same peer community. For example, the analytics engine 110 may assign, to each clinician in the same peer community, a rank corresponding to how much the activity patterns of the clinician deviate from a synthetic norm and/or an expected norm for that peer community. The expected norms for the peer community may be determined based on the activity patterns of at least a portion of the clinicians included in the peer community. Meanwhile, instead of or in addition to the activity patterns of the clinicians in the peer community, the synthetic norm for the peer community may be generated based on additional data including, for example, medical protocol, generalized observations, and/or the like. The analytics engine 110 may determine that a clinician exhibits anomalous behavior if the clinician is ranked above or below a threshold value.

The analytics engine 110 may receive other input data that does not originate with the data systems 120. The other input data may include additional signals that can be used to detect peer communities or anomalies. The other input data may include information to trigger assessment of communities and behavior. For example, a user interface may be presented to collect configuration parameters and initiate assessment of the information received from the data system 120 by the analytics engine 110. In some implementations, the other input data may be received from a time and attendance system. For example, when a clinician clocks out to indicate the end of a shift, the analytics engine 110 may receive a message identifying the clinician clocking out. Because this may indicate a new batch of transaction may be ready for processing, the analytics engine 110 may initiate one or more of the processes described. In some implementations, the analytics engine 110 may assess the transactions from the current shift and provide a response to the time and attendance system. In this way, the clinician may be presented with a message including positive reinforcement if the transactions were consistent with best practices (or at least non-divergent). In the event that the clinician's shift included a questionable transaction or behaviors indicating potential diversion, the message may cause collection of additional information near in time to the transaction(s) in question. The collection may include initiating an investigation workflow as described. The collection may include additional information used to identify the communities of clinicians. Patient history from repository.

Figure 2:
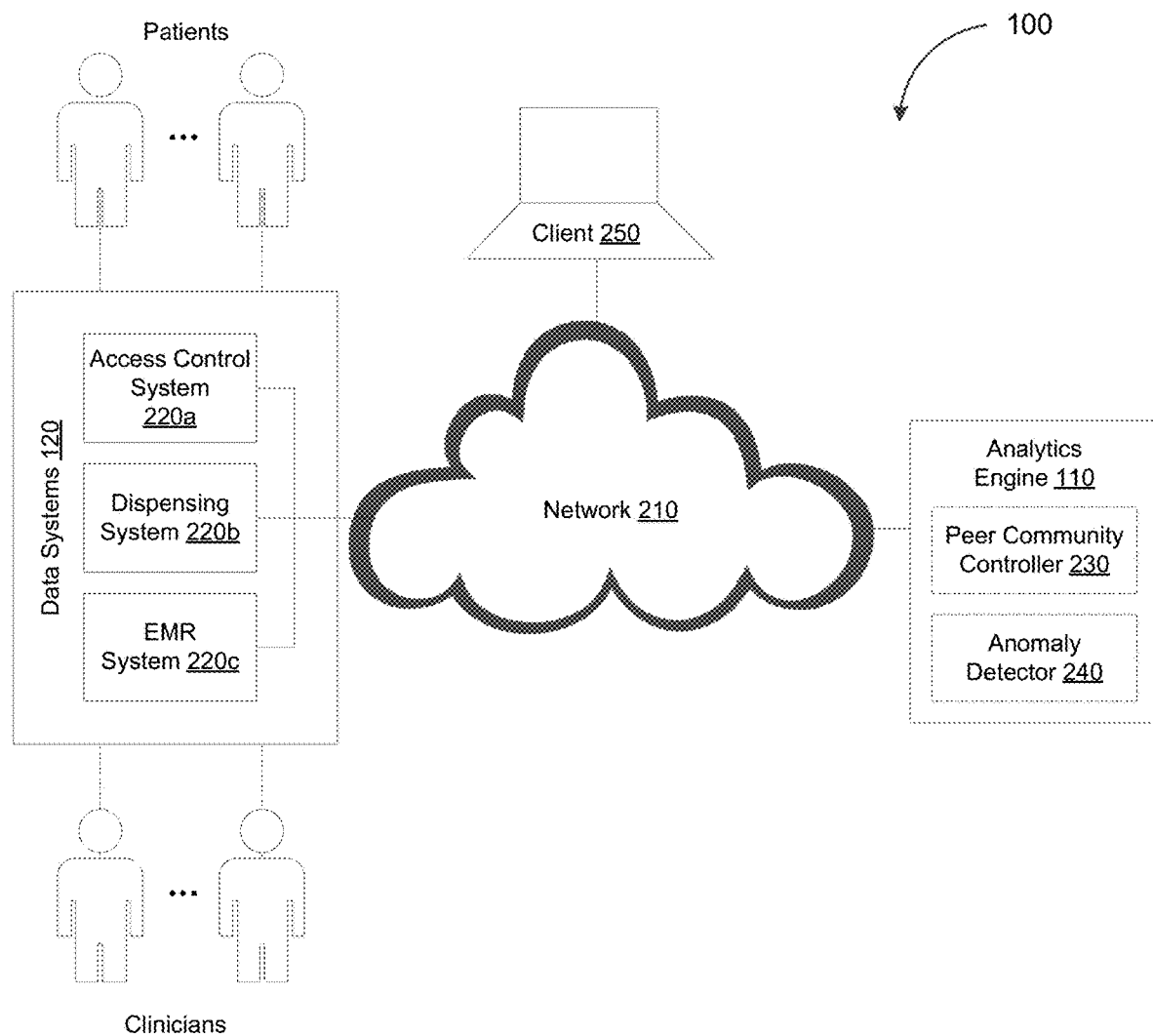
FIG. 2 depicts a system diagram illustrating an example of a clinician tracking system, in accordance with some example embodiments.

FIG. 2 depicts a system diagram illustrating an example of the clinician tracking system 100, in accordance with some example embodiments. As shown in FIG. 2, the analytics engine 110 and the one or more data systems 120 may be communicatively coupled via a network 210. The network 210 may be any wired and/or wireless network including, for example, a public land mobile network (PLMN), a local area network (LAN), a virtual local area network (VLAN), a wide area network (WAN), the Internet, and/or the like.

In the example shown in FIG. 2, the one or more data systems 120 may include an access control system 220a, a dispensing system 220b, and an electronic medical record (EMR) system 220c. As noted, a clinician interacting with the access control system 220a, the dispensing system 220b, and/or the electronic medical record system 220c may trigger the generation of one or more corresponding transaction records. For example, the clinician dispensing a medication from a dispensing cabinet may trigger the generation of a transaction record that includes a timestamp, a clinician identifier of the clinician, a device identifier of the dispensing cabinet, a patient identifier of a patient prescribed the medication, an identifier of the medication retrieved from the dispensing cabinet, a quantity of the medication retrieved from the medication cabinet, and/or the like. Alternatively and/or additionally, a clinician using an infusion pump to administer a medication to a patient may trigger the generation of a transaction record that includes a timestamp, a clinician identifier of the clinician, a device identifier of the infusion pump, a patient identifier of the patient receiving the medication, an identifier of the medication being administered to the patient, a quantity of the medication being administered to the patient, and/or the like.

Referring again to FIG. 2, the analytics engine 110 may include a peer community controller 230 and an anomaly detector 240. As noted, the analytics engine 110 may receive, from the one or more data systems 120, a plurality of input data that include at least a portion of the transaction records generated by the one or more data systems 120 in response to interactions between the one or more data systems 120 and a plurality of different clinicians. Moreover, the input data from the one or more data systems 120 may correspond to attributes that may be used to identify different peer communities of clinicians. Accordingly, the peer community controller 230 may identify, based at least on the input data received from the one or more data systems 120, peer communities of clinicians who should exhibit the same and/or similar activity patterns. For instance, in some example embodiments, the peer community controller 230 may identify, based at least on the input data received from the one or more data systems 120, peer communities of clinicians who treat the same patients. Alternatively and/or additionally, the peer community controller 230 may identify, based at least on the input data received from the one or more data systems 120, peer communities of clinicians who interact with the same medical devices and/or medical devices in a same care area such as, for example, medical-surgical, intensive care, emergency, non-acute, observation, outpatient, infusion center, and/or the like.

In some example embodiments, the anomaly detector 240 may be configured to determine whether a clinician exhibits anomalous behavior by comparing the activity patterns of the clinician to the activity patterns of other clinicians in the same peer community. As noted, the activity patterns of the clinician may include a series of transaction records, which generated when the clinician interacts with the one or more data systems 120. The series of transaction records may be divided temporally to correspond, for example, to the shifts associated with the clinician. The anomaly detector 240 may determine that the clinician exhibits anomalous behavior if the activity patterns of the clinician deviate from the activity patterns of other clinicians in the same peer community. For instance, the clinician may be assigned a rank corresponding to how much the activity patterns of the clinician deviate from the expected norms for the peer community of the clinician. The anomaly detector 240 may determine that a clinician exhibits anomalous behavior if the clinician is ranked above or below a threshold value. The determination may be based on a single behavior score or a combination of scores over a period of time (e.g., average or moving average). In some implementations, the ranking may be assessed using a range of acceptable scores. In some implementations, the threshold value or range may be dynamically generated. For example, as a system collects behavior information for specific communities, the threshold value or range may be generated to reflect the community. In some implementations, the system may include absolute limits for the threshold value or range to prevent an entire community of diverters from escaping detection. A user interface may be provided to receive such configurations for the anomaly detect 240 such as the described threshold values or ranges.

In some example embodiments, the anomaly detector 240 may respond the identification of a clinician exhibiting anomalous behavior by at least triggering an investigative workflow. The investigative workflow may include the anomaly detector 240 generating an alert identifying the clinician exhibiting anomalous behavior and sending the alert to a client 250 via the network 210. Furthermore, the investigative protocol may include the anomaly detector 240 configuring one or more of the data systems 120. For instance, the anomaly detector 240 activate one or more surveillance devices (e.g., video cameras, still image cameras, audio recorders, and/or the like) at a medical device (e.g., dispensing cabinet, infusion pump, wasting station, and/or the like) whenever the clinician accesses the medical device. Alternatively and/or additionally, the anomaly detector 240 may configure the medical device to isolate medication accessed by the clinician. For example, the anomaly detector 240 may activate a surveillance device at a wasting station in response to the clinician accessing the wasting station to dispose of unused medication. Moreover, the anomaly detector 240 may configure the wasting station to isolate the unused medication returned by the clinician, for example, in a designated receptacle that is separate from the receptacles holding unused medication returned by other clinicians.

Figure 3A:
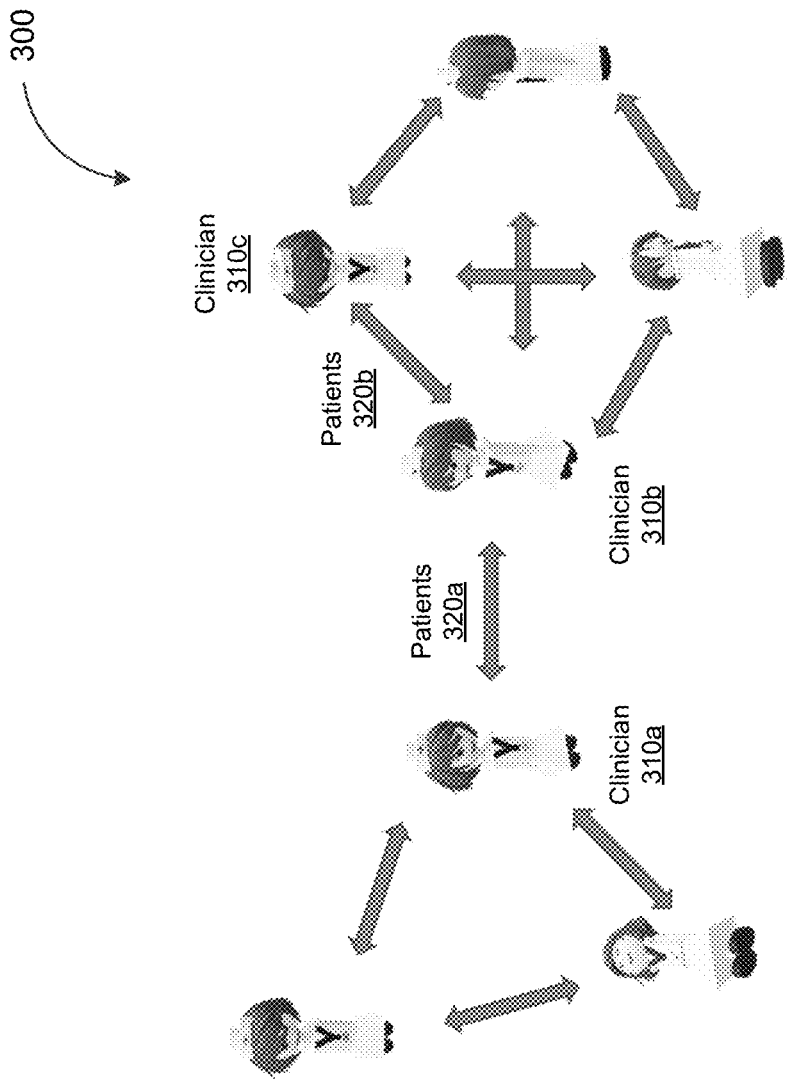
FIG. 3A depicts a graph representative of an example of a peer network, in accordance with some example embodiments.

As noted, the analytics engine 110, for example, the peer community controller 230, may be configured to identify one or more peer communities of clinicians, each of which including clinicians who should exhibit the same and/or similar activity patterns. In some example embodiments, the peer community controller 230 may form, based at least on one or more attributes associated with each clinician, a peer network of clinicians before identifying the peer communities that are present in the peer network. To further illustrate, FIG. 3A depicts a graph representative of a peer network 300, in accordance with some example embodiments. As shown in FIG. 3A, the peer network 300 may include a plurality of nodes connected by a plurality of edges. In some example embodiments, each node in the peer network 300 may correspond to a clinician including, for example, a first clinician 310a, a second clinician 310b, a third clinician 310c, and/or the like. Meanwhile, each edge in the peer network 300 may connect two nodes and may therefore correspond to a common attribute shared between the clinicians corresponding to the two nodes connected by the edge. The peer community controller 230 may form the peer network 300 by at least identifying clinicians who share common attributes (e.g., nodes that should be interconnected by an edge) and/or clinicians who do not share any common attributes (e.g., nodes that should not be left unconnected).

For instance, the peer community controller 230 may determine that two nodes should be interconnected by an edge if the clinicians corresponding to the nodes treat at least one common patient. Accordingly, the edge connecting the first clinician 310a and the second clinician 310b may correspond to one or more patients 320a who are treated by the first clinician 310a as well as the second clinician 310b. Meanwhile, the edge connecting the second clinician 310b and the third clinician 310c may correspond to one or more patients 320b who are treated by the second clinician 310b as well as the third clinician 310c. It should be appreciated that each edge in the peer network 300 may be associated with a weight representative of strength the affiliation between the nodes connected by the edge. In the example shown in FIG. 3A, the weight associated with an edge in the peer network 300 may correspond to a quantity of patients treated by the clinicians associated with the two nodes connected by the edge.

The peer network 300 may include multiple peer communities. The peer community controller 230 may apply one or more supervised and/or unsupervised machine learning technique to identify the peer communities present in the peer network 300. For instance, the peer community controller 230 may apply a neural network trained to identify the peer communities present in the peer network 300. Alternatively and/or additionally, the peer community controller 230 may also apply alternate techniques including, for example, minimum cut, hierarchical clustering, Girvan-Newman, modularity maximization, clique detection, and/or the like. Nevertheless, in some example embodiments, the peer community controller 230 may be required to generate the peer network 300 based on multiple attributes before the nodes in the peer network 300 form discernable peer communities.

Figure 3B:
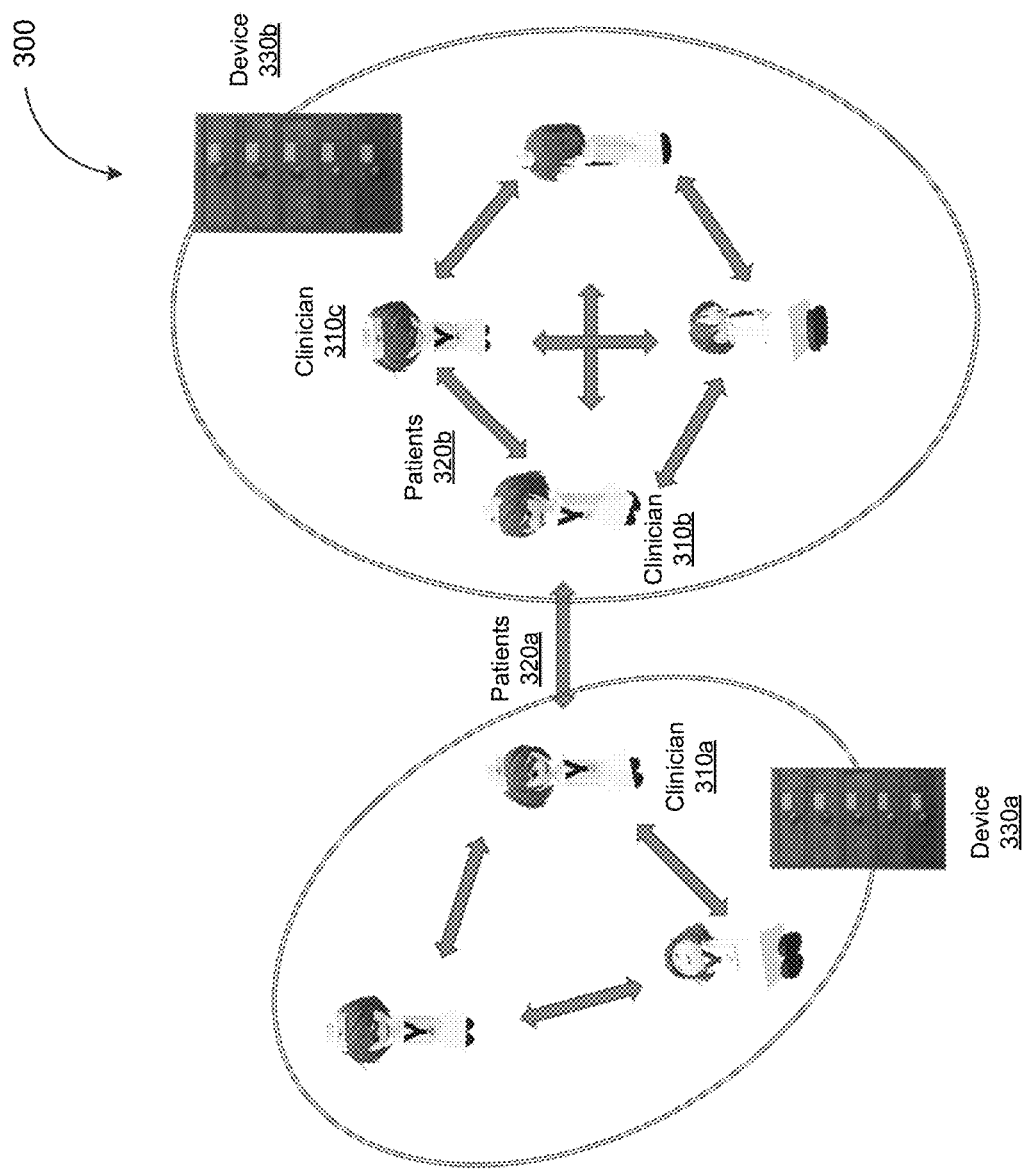
FIG. 3B depicts a graph representative of an example of a peer network, in accordance with some example embodiments.

To further illustrate, FIG. 3B shows the peer network 300 being further refined by applying the medical devices that each of the clinicians in the peer network 300 interacts with. As noted, since clinicians operating in close proximity (e.g., in the same care area and/or the like) should exhibit the same and/or similar activity patterns, the location of medical devices may impose a geographical constraint on membership in each peer community. For instance, as shown in FIG. 3B, in addition to treating the same patients, the first clinician 310a may be further interconnected with one or more other clinicians who interact with the same medical devices and/or medical devices located in a same care area such as, for example, a first device 330a. Likewise, the second clinician 310b and the third clinician 310c may be interconnected with other clinicians who not only treat the same patients but also interact with the same medical devices and/or medical devices located in a same care area such as, for example, a second device 330b. Moreover, as shown in FIG. 3B, while the first clinician 310a and the second clinician 310b may be interconnected because the first clinician 310a and the second clinician 310b treat one or more of the same patients, the first clinician 310a and the second clinician 310b may nevertheless be grouped into separate peer communities based on one or more other attributes including, as shown in FIG. 3B, the medical devices being used by the first clinician 310a and the second clinician 310b. As noted, the care areas in which the first clinician 310a and the second clinician 310b operate may be indicative of the conditions of the patients being treated by the first clinician 310a and the second clinician 310b. Accordingly, while the first clinician 310a and the second clinician 310b may have both treated the same patients, the first clinician 310a and the second clinician 310b may have treated these patients at different points of their care. For example, the first clinician 310a may have treated a patient while that patient was first admitted for emergency care while the second clinician 310b may have treated the same patient but after the patient has stabilized and transitioned to intensive care. Thus, FIG. 3B shows the first clinician 310a and the second clinician 310b as being interconnected but members of different peer communities.

Figure 3C:
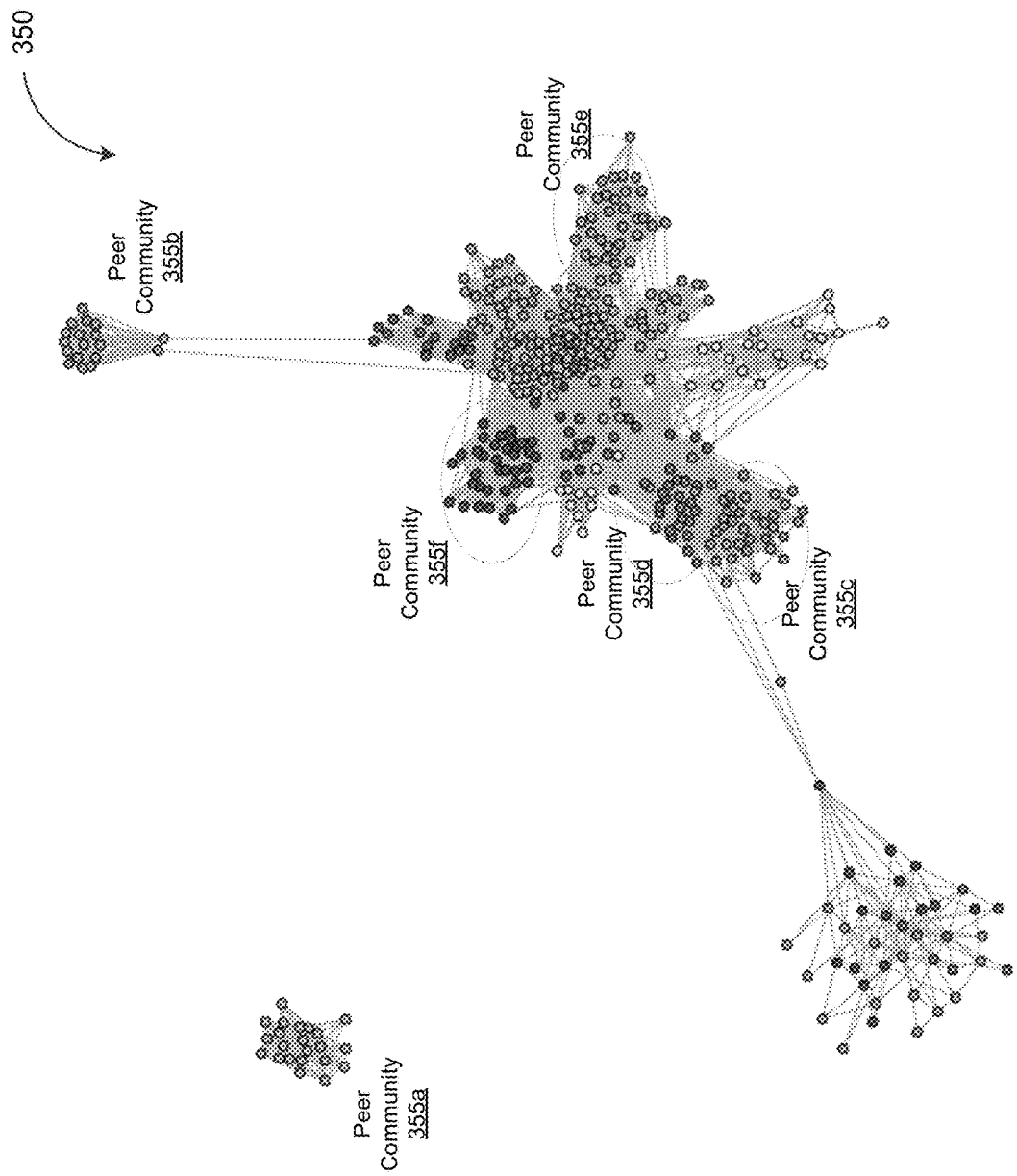
FIG. 3C depicts a graph representative of another example of a peer network, in accordance with some example embodiments.

FIG. 3C depicts a graph illustrating another example of a peer network 350, in accordance with some example embodiments. As shown in FIG. 3C, the peer network 350 may include a plurality of peer communities including, for example, a first peer community 355a, a second peer community 335b, a third peer community 335c, a fourth peer community 335d, a fifth peer community 335e, a sixth peer community 335f, and/or the like. As noted, clinicians in the same peer community may share common attributes and may therefore have the same and/or similar activity patterns whereas clinicians in different peer communities may have different attributes and different activity patterns. Nevertheless, it should be appreciated that a clinician may exhibit varying degrees of affiliation to multiple peer communities. Accordingly, as shown in FIG. 3C, different peer communities such as, for example, the third peer community 335c and the fourth peer community 335d, may overlap due to clinicians are affiliated with multiple peer communities. To segregate overlapping peer communities, the peer community controller 230 may apply additional attributes that differentiate between clinicians who belong to one peer community but not another peer community.

One technique for identifying the multitude of peer communities present in a peer network such as, for example, the peer network 350 may rely on the statistical relationship between community membership and clinician attributes in order to infer community membership based on the attributes of each clinician as well as the attributes of each clinician based on individual community membership. For instance, a peer network G may include an N quantity of nodes. Each of the N quantity of nodes may correspond to a clinician having a K quantity of attributes denoted by X, wherein $X_{uk}$ may correspond to the k-th attribute of the node u. The K quantity of attributes may include, for example, the patients treated by the clinician, the medical devices that the clinician interacts with, and/or the like. Meanwhile, the peer network G may include a C quantity of peer communities. For community memberships F, each node u may be associated with a non-negative affiliation weight $F_{uc} \in [0, \infty)$ to an individual peer community c. Accordingly, node u does not belong to peer community c when $F_{uc}=0$.

In some example embodiments, the peer community controller 230 may construct a graph G (V, E) based on community membership F. To represent the graph G (V, E), the peer community controller 230 may generate an adjacency matrix $A \in \{0,1\}^{N \times N}$ to represent the graph G(V, E) using a probabilistic generative process to detect overlapping peer communities. That is, the value of each entry $A_{uv} \in \{0,1\}$ in the adjacency matrix A may correspond to whether the graph G includes an edge interconnecting the node u and the node v. For instance, Equation (1) below may express the probability $P_{uv}$ that two nodes u and v belonging to a community c are connected.

$$P_{uv}(c) = 1 - \exp(-F_{uc} \cdot F_{vc}) \tag{1}$$

wherein $F_{uc}$ may denote the affiliation weight between the node u and the peer community c while $F_{uc}$ may denote the affiliation weight between the node v and the peer community c.

In accordance with Equation (1), if either the node u or the node v does not belong to the peer community c (e.g., $F_{uc} = 0$ or $F_{vc} = 0$), then the probability of the node u and the node v being connected would be zero. Furthermore, in order for the graph G to not include any edges interconnecting the node u or the node v, the node u or the node v may not be connected in any community u. The probability of the node u and the node v being unconnected in the graph G may be expressed by Equation (2) below:

$$1 - P_{uv} = \Pi_c(1 - P_{uv}(c)) = \exp(-\Sigma_c F_{uc} \cdot F_{vc}) \tag{2}$$

Accordingly, the value of each entry $A_{uv} \in \{0,1\}$ in the adjacency matrix A representative of the graph G may be determined in accordance with the following Equations (3) and (4):

$$P_{uv} = 1 - \exp(-\Sigma_c F_{uc} \cdot F_{vx}) \tag{3}$$

$$A_{uv} \sim \text{Bernoulli}(P_{uv}) \tag{4}$$

As noted, an edge in the graph G that interconnects the node u and the node v may correspond to one or more common attributes shared by the clinicians associated with each of the node u and the node v. The common attributes shared between the node u and the node v may determine the nodes' membership in the peer community c. Moreover, the attributes that are associated with each of the nodes u and v may also be inferred by the nodes' membership in the peer community c. For instance, Equations (5) and (6) below expresses the probability $Q_{uk}$ of the node u being associated with an attribute k based on the probability $F_{uc}$ of the node u being a member the peer community c:

$$Q_{uk} = \frac{1}{1 + \exp\left(-\sum_c W_{kc} \cdot F_{uc}\right)}, \tag{5}$$

$$X_{uk} \sim \text{Bernoulli}(Q_{uk}) \tag{6}$$

wherein $W_{kc}$ may denote a real-valued logistic model parameter for community c to the k-th node attribute and $W_{k(C+1)}$ may denote a bias term. The value of $W_{kc}$ may represent the correlation between the node u being a member of the peer community c and the node u being associated with the attribute k.

To identify the peer communities that are present in the graph G (V, E) as represented by the adjacency matrix A, the peer community controller 230 may infer, based on the graph G, the values of latent variables F and W. Accordingly, the peer community controller 230 may be required to estimate N·C community memberships (i.e., $\hat{F} \in \mathbb{R}^{N \times C}$) and K·(C+1) logistic weight parameters (i.e., $\hat{W} \in \mathbb{R}^{K \times (C+1)}$). To do so, the peer community controller 230 may determine, for $\hat{F}$ and $\hat{W}$, optimal values that maximizes the likelihood l(F, W)=log P(G, X|F,W) of the observed data G, X in accordance with Equation (7) below:

$$\hat{F}, \hat{W} = \underset{F \geq 0, W}{\operatorname{argmax}} \log P(G, X \mid F, W). \tag{7}$$

Because G and X are conditionally independent given F and W, the log-likelihood log P(G, X|F,W) may be decomposed in accordance with Equation (8) below:

$$\log P(G, X|F,W) = \mathcal{L}_G + \mathcal{L}_X \tag{8}$$

wherein $\mathcal{L}_G = \log P(G|F)$ and $\mathcal{L}_X = \log P(X|F,W)$.

Based on Equations (3)-(6) above, the peer community controller 230 may compute $\mathcal{L}_G$ and $\mathcal{L}_X$ as shown in Equations (9) and (10) below:

$$\mathcal{L}_G = \Sigma_{(u,v) \in E} \log(1 - \exp(-F_u F_v^T)) - \Sigma_{(u,v) \notin E} F_u F_v^T \tag{9}$$

$$\mathcal{L}_X = \Sigma_{u,k}(X_{uk} \log Q_{uk} + (1 - X_{uk}) \log(1 - Q_{uk})) \tag{10}$$

wherein $F_u$ may be a vector $\{F_{uc}\}$ for node u and $Q_{uk}$ may be defined in accordance with Equations (3) and (4).

The peer community controller 230 may further invoked $l_1$-regularization on W to avoid overfitting and to learn sparse relationships between communities and attributes. Accordingly, the peer community controller 230 may be required to solve the optimization problem expressed by Equation (11) below:

$$\hat{F}, \hat{W} = \underset{F \geq 0, W}{\operatorname{argmax}} \mathcal{L}_G + \mathcal{L}_X - \lambda |W|_1 \tag{11}$$

wherein $\lambda$ may denote a regularization hyperparameter.

The solve the optimization problem set forth in Equation (11), the peer community controller 230 may apply a block coordinate ascent approach in which the value of $F_u$ is updated for each node u by at least fixing W and community membership $F_v$ for all other nodes v. Once $F_u$ is updated for all nodes, the peer community controller 230 may update W while fixing community memberships F.

To update community membership $F_u$ for an individual node u while fixing all other parameters such as, for example, the peer community membership $F_v$ for other nodes v and the logical model parameters W, the peer community controller 230 may be required to solve the convex subproblem expressed by Equation (12) below:

$$\hat{F}_u = \underset{F_{uc} \geq 0}{\operatorname{argmax}} \mathcal{L}_G(F_u) + \mathcal{L}_X(F_u) \tag{12}$$

wherein $\mathcal{L}_G(F_u)$ and $\mathcal{L}_X(F_u)$ include portions of $\mathcal{L}_G$ and $\mathcal{L}_X$ involving $F_u$ as shown by Equations (13) and (14) below:

$$\mathcal{L}_G(F_u) = \Sigma_{v \in N(u)} \log(1 - \exp(-F_u F_v^T)) - \Sigma_{v \notin N(u)} F_u F_v^T, \tag{13}$$

$$\mathcal{L}_X(F_u) = \Sigma_k(X_{uk} \log Q_{uk} + (1 - X_{uk}) \log(1 - Q_{uk})) \tag{14}$$

wherein N(u) may denote a set of neighbors of the node u. Note that the problem expressed by Equations (11) and (12)

may be a convex problem where as $\mathcal{L}_G(F_u)$ is a concave function of $F_u$ and $\mathcal{L}_X(F_u)$ is a logistic function of $F_{uc}$ when W is fixed.

To solve the convex problem, the peer community controller 230 may apply projected gradient descent computed in accordance with Equations (15) and (16) below:

$$\frac{\partial \mathcal{L}_G(F_U)}{\partial F_u} = \sum_{v \in N(u)} F_{vc} \frac{\exp(-F_u F_v^T)}{1 - \exp(-F_u F_v^T)} - \sum_{v \notin N(u)} F_{vc}, \quad (15)$$

$$\frac{\partial \mathcal{L}_X(F_u)}{\partial F_u} = \sum_k (X_{uk} - Q_{uk}) W_{ck}. \quad (16)$$

The peer community controller 230 may update each $F_{uc}$ to correspond to the probability of the node u being a member of the peer community c. For instance, each $F_{uc}$ may be updated by gradient descent before being projected onto a space of non-negative real numbers [0, ∞) in accordance with Equation (17) below:

$$F_{uc}^{new} = \max\left(0, F_{uc}^{old} + \alpha\left(\frac{\partial \mathcal{L}_G(F_u)}{\partial F_u} + \frac{\partial \mathcal{L}_X(F_u)}{\partial F_u}\right)\right) \quad (17)$$

wherein α may correspond to a learning rate which may be set using backtracking line search.

Once the peer community controller 230 has learned the real-valued community affiliations F, the peer community controller 230 may determine whether node u actually belongs to the peer community c. To do so, the peer community controller 230 may impose a threshold δ such that the node u may be a member of the peer community c if the corresponding probability $F_{uc}$ of the node u being a member of the peer community c exceeds the threshold δ. The value of the threshold δ may be set such that the node u may be a member of the peer community c if the probability of the node u being connected to another node that is a member of the peer community c is greater than $$\frac{1}{N},$$

wherein N may correspond to a total quantity of nodes in the graph G.

In some example embodiments, the value of the threshold δ may be determined based on Equations (18) and (19) below:

$$\frac{1}{N} \leq 1 - \exp(-\delta^2), \quad (18)$$

$$\delta = \sqrt{-\log(1 - 1/N)}. \quad (19)$$

Referring again to FIG. 3C, the peer community controller 230 may be configured to identify the plurality of peer communities present in the peer network 350 including, for example, the first peer community 355a, the second peer community 335b, the third peer community 335c, the fourth peer community 335d, the fifth peer community 335e, the sixth peer community 335f, and/or the like. Each of the peer community present in the peer network 350 may correspond to a group of clinicians who share sufficiently similar attributes and should therefore exhibit the same and/or similar activity patterns. For instance, each peer community present in the peer network 350 may correspond to clinicians who treat the same patients as well as interact with the same medical devices and/or medical devices located in the same care area. By identifying the peer communities of clinicians who share these common attributes, the peer community controller 230 may be able to differentiate between clinicians who have been assigned different shifts, care areas, and/or tasks such as, for example, permanent clinicians, floating clinicians, supplemental clinicians, student clinicians, and charge clinicians. As noted, a permanent nurse, float nurse, a supplemental nurse, a student nurse, and a charge nurse may also exhibit different activities patterns because of differences in assigned shifts, care areas, and/or tasks. Accordingly, by grouping clinicians who have been assigned different shifts, care areas, and/or tasks into the appropriate peer communities, the peer community controller 230 may ensure the anomaly detector 240 comparing the activity patterns of clinicians who have been assigned the same and/or similar shifts, care areas, and/or tasks.

Figure 4:
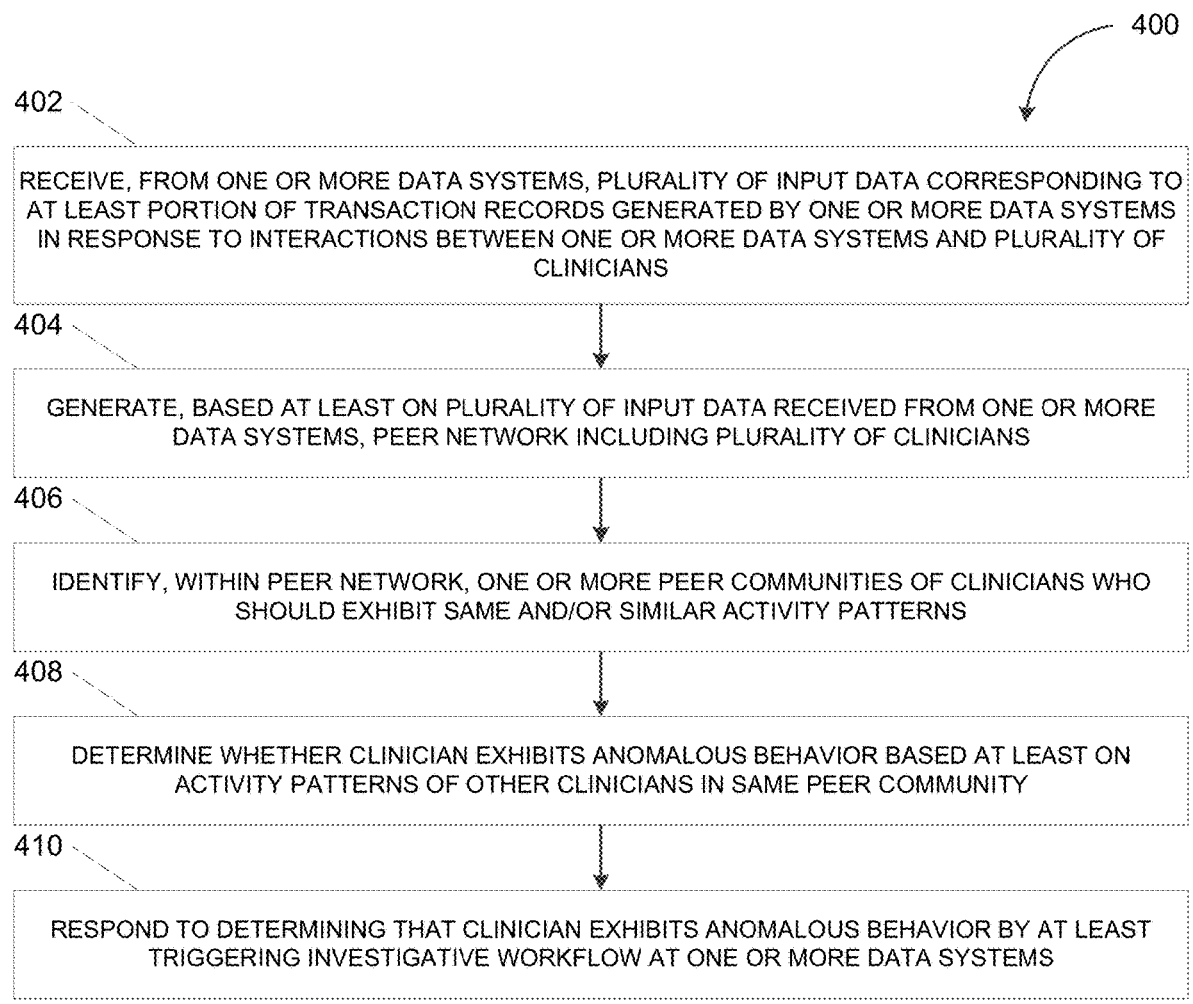
FIG. 4 depicts a flowchart illustrating a process for tracking clinician behavior, in accordance with some example embodiments.

FIG. 4 depicts a flowchart illustrating a process 400 for tracking clinician behavior, in accordance with some example embodiments. Referring to FIGS. 1-2, 3A-C, and 4, the process 400 may be performed, in whole or in part, by the analytics engine 110.

At 402, the analytics engine 110 may receive, from the one or more data systems 120, a plurality of input data corresponding to at least a portion of transaction records generated by the one or more data systems 120 in response to interactions between the one or more data systems 120 and a plurality of clinicians. For instance, as shown in FIG. 2, the one or more data systems 120 may include the access control system 220a, the dispensing system 220b, and the electronic medical record (EMR) system 220c. Furthermore, as noted, the one or more data systems 120 may include medical devices such as, for example, dispensing cabinets, infusion pumps, wasting stations, and/or the like. The one or more data systems 120 may generate a transaction record when a clinician interacts with the one or more data systems. At least a portion of the transaction records generated by the one or more data systems 120 may be sent as input data to the analytics engine 110. In some implementations, the transaction records may be normalized to allow meaningful comparison of attributes. For example, one system may refer to patients using a field named "PATIENT" while another system may refer to patients using a field named "PATIENT_ID". The normalization may be performed by the analytics engine 110 as a pre-processing step or by another system within the environment. The normalization may be performed according to a standardized messaging format such as a Health Level Seven (HL7) format or other electronic record format. The normalization can provide enable a comparison between common, analogous, and/or semantically equivalent attributes from different transactions.

For example, a clinician dispensing a medication from a dispensing cabinet may trigger the generation of a transaction record that includes a timestamp, a clinician identifier of the clinician, a device identifier of the dispensing cabinet, a patient identifier of a patient prescribed the medication, an identifier of the medication retrieved from the dispensing cabinet, a quantity of the medication retrieved from the medication cabinet, and/or the like. Alternatively and/or additionally, a clinician using an infusion pump to administer a medication to a patient may trigger the generation of a transaction record that includes a timestamp, a clinician identifier of the clinician, a device identifier of the infusion pump, a patient identifier of the patient receiving the medication, an identifier of the medication being administered to the patient, a quantity of the medication being administered to the patient, and/or the like.

At 404, the analytics engine 110 may form, based at least on the plurality of input data received from the one or more data systems 120, a peer network including the plurality of clinicians. In some example embodiments, the analytics engine 110 may form, for example, the peer network 300, based on one or more attributes associated with a plurality of clinicians including, for example, the patients treated by each clinician, the medical devices each clinician interacts with, and/or the like. For instance, the analytics engine 110 may form the peer network 300 by at least interconnecting a plurality of nodes corresponding to clinicians with edges that correspond to common attributes shared between the clinicians. In the example shown in FIG. 3A, the edges may correspond to one or more patients who treated by the clinicians corresponding to the nodes interconnected by the edges. Meanwhile, FIG. 3B shows that in addition to treating the same patients, the nodes in the peer network 300 may be further interconnected based on the corresponding clinicians interacting with the same medical devices and/or medical devices located in a same care area.

At 406, the analytics engine 110 may identify, within the peer network, one or more peer communities of clinicians who should exhibit the same and/or similar activity patterns. In some example embodiments, the analytics engine 110 may identify, in the peer network 300, one or more peer communities of clinicians who share sufficiently similar attributes such that the clinicians in the same peer community should also exhibit the same and/or similar activity patterns. For example, as noted, the analytics engine 110 may apply a machine learning model trained to identify the one or more peer communities of clinicians that are present in, for example, the peer network 300. Alternatively and/or additionally, the analytics engine may 110 identify the peer communities by applying an alternate technique such as, for example, minimum cut, hierarchical clustering, Girvan-Newman, modularity maximization, clique detection, and/or the like.

At 408, the analytics engine 110 may determine whether a clinician exhibits anomalous behavior based at least on the activity patterns of other clinicians in a same peer community. For example, the analytics engine 110 may be configured to determine whether a clinician exhibits anomalous behavior by comparing the activity patterns of the clinician to the activity patterns of other clinicians in the same peer community. In some example embodiments, the activity patterns of the clinician may include a series of transaction records, which generated when the clinician interacts with the one or more data systems 120. Furthermore, the series of transaction records may be divided temporally to correspond, for example, to the shifts associated with the clinician. The analytics engine 110 may determine that the clinician exhibits anomalous behavior if the activity patterns of the clinician deviate from the activity patterns of other clinicians in the same peer community. For instance, the analytics engine 110 may assign, to the clinician, a rank corresponding to how much the activity patterns of the clinician deviate from the expected norms for the peer community of the clinician. The analytics engine 110 may determine that the clinician exhibits anomalous behavior if the clinician is ranked above or below a threshold value.

At 410, the analytics engine 110 may respond to determining that the clinician exhibits anomalous behavior by at least triggering an investigative workflow at one or more of the data systems 120. For example, the investigative workflow may include the analytics engine 110 generating and sending an alert to the client 250 via the network 210. Alternatively and/or additionally, the investigative workflow may include the analytics engine 110 configuring the one or more data systems 120 to activate one or more surveillance devices at the medical devices accessed by the clinician and/or isolate medication accessed by the clinician. For instance, the analytics engine 110 may configure a dispensing cabinet to activate one or more surveillance devices (e.g., video cameras, still image cameras, audio recorders, and/or the like) whenever the clinician accesses the dispensing cabinet to retrieve medication. Alternatively and/or additionally, the analytics engine 110 may configure a wasting station to isolate unused medication that the clinician disposes at the wasting station. For instance, instead of a shared receptacle that comingles unused medication disposed by multiple clinicians, the wasting station may be configured to provide the clinician with a separate receptacle.

In some implementations, triggering the investigative workflow may include activating a sensor or other collection device within the clinician tracking system 100. The activation may include transmitting a control message to a device to configure the device to initiate collection of information for the investigative workflow such as biometrics of the target of the investigation, electronic medical records for patients interacted with by or near the target of the investigation, location information for the target during one or more shifts, peer clinician information (e.g., peers working with or near to the target), etc. This can be particularly useful to collect information without necessarily alerting a target of the investigation of the investigation. If the target of the investigation were made aware of the data collection, the target of the investigation may alter behavior or take further steps to avoid detection or undermine the integrity of the investigation. Such features provide a technical solution to ensure efficiency and reliability of the investigative workflow.

Figure 5:
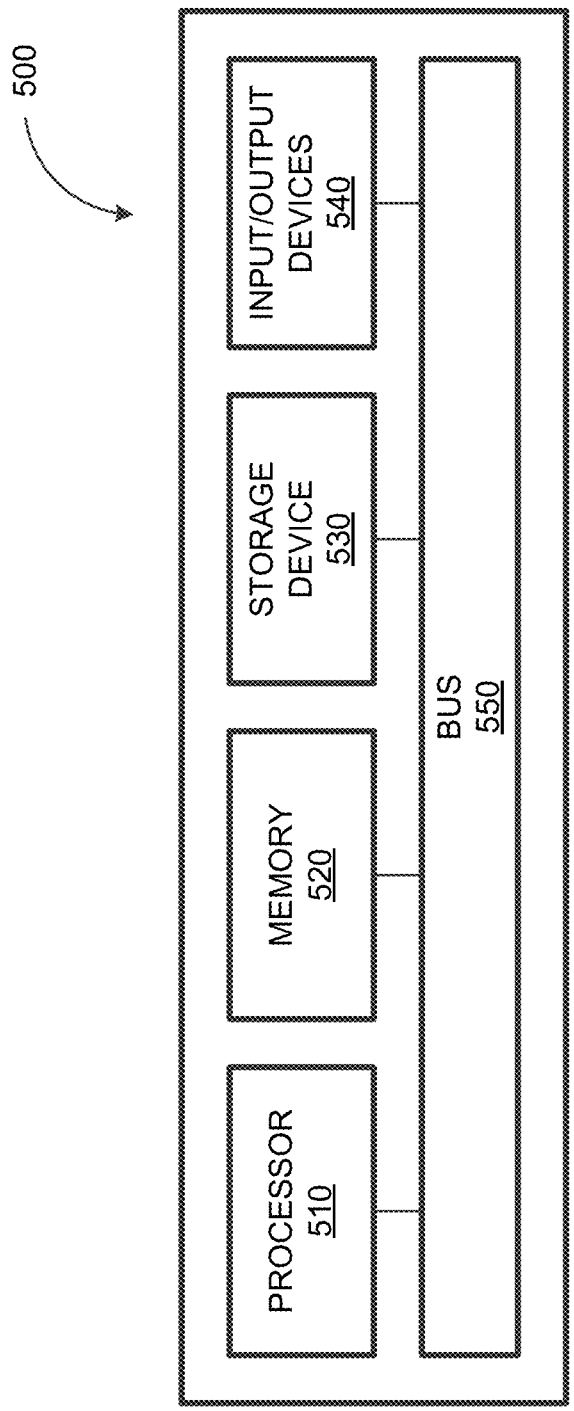
FIG. 5 depicts a block diagram illustrating a computing system, in accordance with some example embodiments.

FIG. 5 depicts a block diagram illustrating a computing system 500 consistent with implementations of the current subject matter. Referring to FIGS. 1 and 2, the computing system 500 can be used to implement the analytics engine 110 and/or any components therein.

As shown in FIG. 5, the computing system 500 can include a processor 510, a memory 520, a storage device 530, and input/output device 540. The processor 510, the memory 520, the storage device 530, and the input/output device 540 can be connected via a system bus 550. The processor 510 is capable of processing specific instructions for execution within the computing system 500 for a peer community based technique for detecting anomalous behavior and dynamically configuring device based thereon. Such executed instructions can implement one or more components of, for example, the analytics engine 110. In some example embodiments, the processor 510 can be a single-threaded processor. Alternatively, the processor 510 can be a multi-threaded processor. The processor 510 is capable of processing instructions stored in the memory 520 and/or on the storage device 530 to display graphical information for a user interface provided via the input/output device 540.

The memory 520 is a computer readable medium such as volatile or non-volatile that stores information within the computing system 500. The memory 520 can store data structures representing configuration object databases, for example. The storage device 530 is capable of providing persistent storage for the computing system 500. The storage device 530 can be a floppy disk device, a hard disk device, an optical disk device, a tape device, a solid-state device, and/or any other suitable persistent storage means. The input/output device 540 provides input/output operations for the computing system 500. In some example embodiments, the input/output device 540 includes a keyboard and/or pointing device. In various implementations, the input/output device 540 includes a display unit for displaying graphical user interfaces.

According to some example embodiments, the input/output device 540 can provide input/output operations for a network device. For example, the input/output device 540 can include Ethernet ports or other networking ports to communicate with one or more wired and/or wireless networks (e.g., a local area network (LAN), a wide area network (WAN), the Internet).

In some example embodiments, the computing system 500 can be used to execute various interactive computer software applications that can be used for organization, analysis and/or storage of data in various formats. Alternatively, the computing system 500 can be used to execute specific peer community anomaly detection software applications. These applications can be used to perform various functionalities within a clinician tracking system (such as shown in FIG. 1), e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 540. The user interface can be generated and presented to a user by the computing system 500 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one specifically configured programmable processor, which can be special or general purpose, coupled to receive data and specific instructions from, and to transmit data and instructions to, a storage system, at least one input device, and at least one output device. The programmable system or computing system may include one or more clients and/or servers. A client and server are generally remote from each other and typically interact through a communication network. The relationship of client and server arises by virtue of computer programs running on the respective computers and having a client-server relationship to each other.

These specific computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible. The term "correspond" or "corresponds" or "corresponding" may include comparing at least two values where the at least two values exactly match, fuzzy match, phonetically match, match within a predetermined tolerance (e.g., plus or minus), match according to a predetermined relationship (e.g., score based on dynamically generated weights), or other measure comparing the at least two values.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
    at least one data processor; and
    at least one memory storing instructions which, when executed by the at least one data processor, result in operations comprising:
        identifying a first peer community in a peer network by at least applying a machine-learning model trained to identify one or more peer communities present in the peer network, the peer network comprising a plurality of clinicians, and the first peer community comprising a first clinician and a second clinician from the plurality of clinicians based at least on the first clinician and the second clinician sharing at least one common attribute;
        generating a comparison between a first activity pattern of the first clinician and a second activity pattern of the second clinician;
        determining, based at least on the comparison between the first activity pattern of the first clinician and the second activity pattern of the second clinician, that the first clinician exhibits anomalous behavior; and
        in response to determining that the first clinician exhibits anomalous behavior, isolating at least one medication accessed by the first clinician in a separate receptacle instead of a shared receptacle that contains medication accessed by the plurality of clinicians.

2. The system of claim 1, wherein the at least one common attribute comprises one or more of a same patient treated by the first clinician and the second clinician.

3. The system of claim 1, wherein the at least one common attribute comprises one or more of a same medical device or medical devices located in a same care area that the first clinician and the second clinician interact with.

4. The system of claim 1, wherein the at least one common attribute comprises one or more of: a prescription order, a clinician role, a shift, a supervisor, an educational background, training, an assigned care area, a medical protocol, and a physical layout of facility.

5. The system of claim 1, wherein the operations further comprise:
    generating the peer network, the peer network comprising a first node corresponding to the first clinician and a second node corresponding to the second clinician, and the peer network further comprising an edge interconnecting the first node and the second node based at least on the first clinician and the second clinician sharing the at least one common attribute.

6. The system of claim 5, wherein the peer network is generated based at least on a plurality of transaction records generated by one or more data systems in response to the first clinician or the second clinician interacting with the one or more data systems.

7. The system of claim 6, wherein the plurality of transaction records comprise at least one transaction record that is generated in response to the first clinician interacting with a medical device to retrieve, administer, or dispose of a medication.

8. The system of claim 7, wherein the at least one transaction record comprises at least one of: a timestamp, a first identifier of the first clinician, a second identifier of a patient associated with the medication, a third identifier of the medication, a fourth identifier of the medical device, a location identifier of the medical device, or a quantity of the medication.

9. The system of claim 1, wherein the operations further comprise:
    in response to determining that the first clinician exhibits anomalous behavior, sending, to a client device, an alert indicating the first clinician as exhibiting anomalous behavior.

10. The system of claim 1, wherein the operations further comprise:
    in response to determining that the first clinician exhibits anomalous behavior, activating one or more surveillance devices at a medical device in response to the first clinician interacting with the medical device.

11. The system of claim 1, wherein the machine-learning model comprises at least one of: a neural network, minimum cut, hierarchical clustering, Girvan-Newman, modularity maximization, or clique detection.

12. The system of claim 5, wherein the edge is associated with a weight corresponding to a quantity of common attributes shared between the first clinician and the second clinician.

13. The system of claim 1, wherein generating the comparison comprises assigning, to the first clinician, a rank corresponding to how much the first activity pattern of the first clinician deviates from a norm of the first peer community, and wherein the first clinician is determined to exhibit anomalous behavior based at least on the rank assigned to the first clinician being above or below a threshold value.

14. The system of claim 13, wherein the norm comprises an expected norm determined based at least on the first activity pattern of the first clinician and the second activity pattern of the second clinician.

15. The system of claim 13, wherein the norm comprises a synthetic norm determined based on data in addition to the first activity pattern of the first clinician and/or the second activity pattern of the second clinician.

16. The system of claim 1, wherein the operations further comprise:
    identifying a second peer community present in the peer network by at least applying the machine learning, the comparison to determine whether the first clinician exhibits anomalous behavior excluding a third activity pattern of a third clinician included in the second peer community.

17. A non-transitory computer readable medium storing instructions, which when executed by at least one data processor, result in operations comprising:
    identifying a first peer community in a first peer network by at least applying a machine-learning model trained to identify one or more peer communities present in the peer network, the peer network comprising a plurality of clinicians, and the first peer community comprising a first clinician and a second clinician from the plurality of clinicians based at least on the first clinician and the second clinician sharing at least one common attribute; and generating a comparison between a first activity pattern of the first clinician and a second activity pattern of the second clinician;

determining, based at least on the comparison between the first activity pattern of the first clinician and the second activity pattern of the second clinician, that the first clinician exhibits anomalous behavior; and in response to determining that the first clinician exhibits anomalous behavior, isolating at least one medication accessed by the first clinician, in a separate receptacle instead of a shared receptacle that contains medication accessed by the plurality of clinicians.

18. The computer readable medium of claim 16, wherein the operations further comprise:

identifying a second peer community present in the peer network by at least applying the machine learning, the comparison to determine whether the first clinician exhibits anomalous behavior excluding a third activity pattern of a third clinician included in the second peer community.

19. An apparatus, comprising:

a storage container;

at least one data processor; and at least one memory storing instructions which, when executed by the at least one data processor, result in operations comprising:

receiving an indication identifying a first clinician as exhibiting anomalous behavior, the first clinician being part of a peer community in a peer network comprising a plurality of clinicians, the peer community being identified by at least applying a machine-learning model trained to identify one or more peer communities present in the peer network, and the first clinician being identified as exhibiting anomalous behavior based at least on a comparison between a first activity pattern of the first clinician and a second activity pattern of a second clinician in the peer community; and in response to the indication, restricting access to the storage container by the first clinician to isolate at least one medication stored in the storage container in a separate receptacle instead of a shared receptacle that contains medication accessed by the plurality of clinicians.

* * * * *